United States Patent
Verhoeven et al.

(10) Patent No.: US 11,213,430 B2
(45) Date of Patent: Jan. 4, 2022

(54) INNER EAR PLUG

(71) Applicant: Cochlear Limited, Macquarie University (AU)

(72) Inventors: Kristien Johanna Maria Verhoeven, Mechelen (BE); Daniel Smyth, Dublin (IE); Marcus Andersson, Mölnlycke (SE); Claudiu G. Treaba, New York, NY (US); Fysh Dadd, Lane Cove (AU)

(73) Assignee: Cochlear Limited, Macquire University (AU)

( * ) Notice: Subject to any disclaimer, the term of this patent is extended or adjusted under 35 U.S.C. 154(b) by 684 days.

(21) Appl. No.: 15/165,165

(22) Filed: May 26, 2016

(65) Prior Publication Data

US 2017/0340485 A1 Nov. 30, 2017

(51) Int. Cl.
*A61F 11/00* (2006.01)
*A61M 31/00* (2006.01)
*A61F 11/04* (2006.01)

(52) U.S. Cl.
CPC ............ *A61F 11/00* (2013.01); *A61F 11/045* (2013.01); *A61M 31/002* (2013.01); *A61M 2210/0662* (2013.01)

(58) Field of Classification Search
CPC .. A61F 11/00; A61F 11/045; A61F 2011/085; A61M 31/002
See application file for complete search history.

(56) References Cited

U.S. PATENT DOCUMENTS

| | | | |
|---|---|---|---|
| 4,353,364 A * | 10/1982 | Woods | A61F 11/08 128/867 |
| 5,421,818 A | 6/1995 | Arenberg | |
| 6,045,528 A | 4/2000 | Arenberg | |
| 6,377,849 B1 | 4/2002 | Lenarz | |
| 6,648,873 B2 | 11/2003 | Arenberg | |
| 6,685,697 B1 | 2/2004 | Arenberg | |
| 6,805,547 B2 | 10/2004 | Hsu | |
| 6,889,094 B1 | 5/2005 | Kuzma et al. | |
| 7,194,314 B1 | 3/2007 | Richter et al. | |
| 7,650,194 B2 | 1/2010 | Fritsch | |

(Continued)

FOREIGN PATENT DOCUMENTS

| CN | 104703650 A | 6/2015 |
|---|---|---|
| WO | 2000033775 A1 | 6/2000 |

(Continued)

OTHER PUBLICATIONS

Wolfgang Arnold, et al., "Novel Slow-and Fast-Type Drug Release Round-Window Microimplants for Local Drug Application to the Cochlea: An Experimental Study in Guinea Pigs", Audiol Neurootol, S. Karger AG, Basel, Munich, Germany, Dec. 7, 2004, pp. 53-63.

(Continued)

*Primary Examiner* — Nathan R Price
*Assistant Examiner* — Justin L Zamory
(74) *Attorney, Agent, or Firm* — Edell, Shapiro & Finnan, LLC

(57) ABSTRACT

Embodiments are generally directed to a securable inner drug delivery plug or stopper that is configured to be inserted into, and secured (retained) within, an opening of the inner ear of an recipient. The securable inner drug delivery plug is configured to deliver drugs directly into the inner ear.

25 Claims, 12 Drawing Sheets

(56) References Cited

U.S. PATENT DOCUMENTS

| | | | |
|---|---|---|---|
| 8,197,461 B1 | 6/2012 | Arenberg | |
| 8,318,817 B2 | 11/2012 | Lichter | |
| 9,033,911 B2 | 5/2015 | de Juan, Jr. et al. | |
| 2003/0060799 A1* | 3/2003 | Arenberg | A61F 11/00 604/514 |
| 2006/0264897 A1 | 11/2006 | Lobl | |
| 2007/0077270 A1* | 4/2007 | Wen | A61F 9/0017 424/423 |
| 2008/0319424 A1* | 12/2008 | Muni | A61B 5/411 604/890.1 |
| 2009/0254163 A1 | 10/2009 | Gibson | |
| 2010/0106134 A1 | 4/2010 | Jolly | |
| 2014/0243795 A1* | 8/2014 | Varner | A61F 9/0017 604/521 |
| 2015/0025509 A1 | 1/2015 | Jolly | |
| 2015/0202161 A1 | 7/2015 | Pierstorff et al. | |

FOREIGN PATENT DOCUMENTS

| | | |
|---|---|---|
| WO | 2012170578 A1 | 12/2012 |
| WO | 2014093875 A1 | 6/2014 |

OTHER PUBLICATIONS

Andrew M. Ayoob, et al., "Expert Opinion—The Role of Intracochlear Drug Delivery Devices in the Management of Inner Ear Disease", Informa UK, Ltd., 2014, pp. 465-479.

International Search Report and Written Opinion in counterpart International Application No. PCT/IB2017/052915, dated Aug. 8, 2017, 14 pages.

* cited by examiner

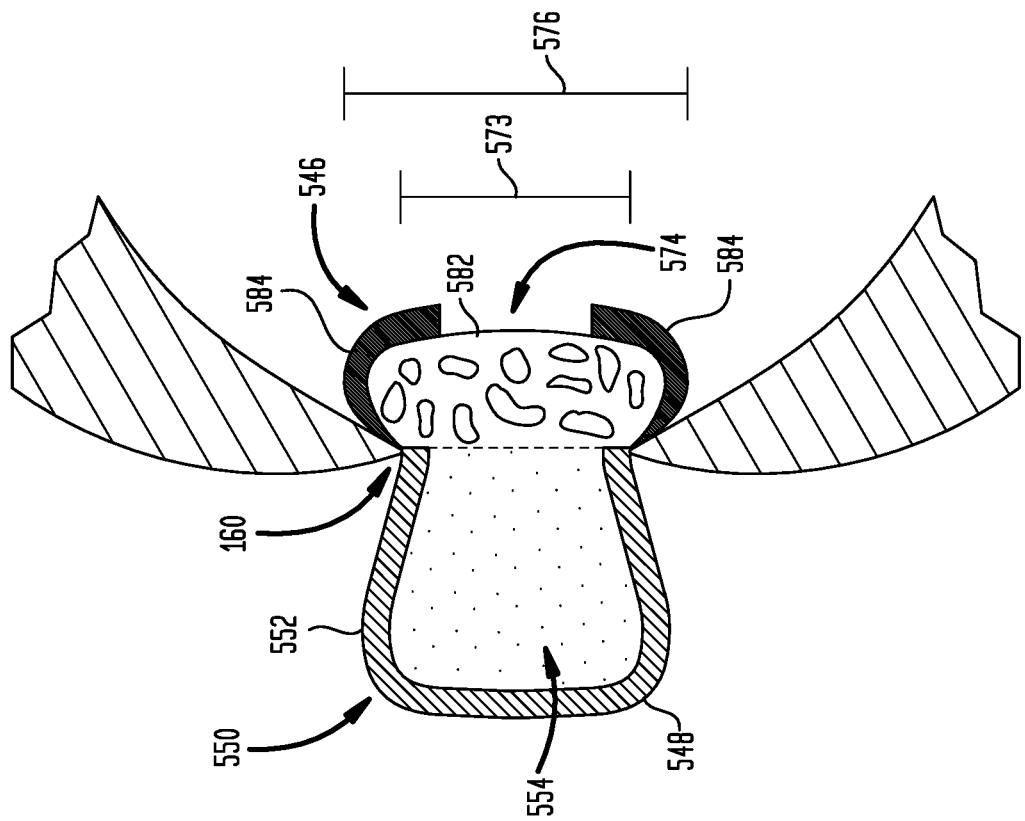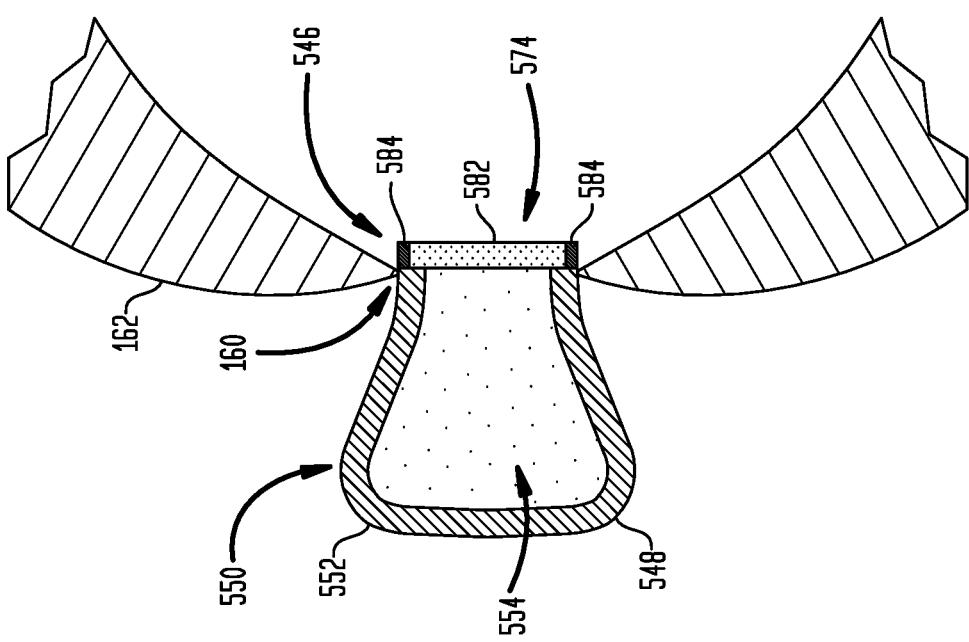

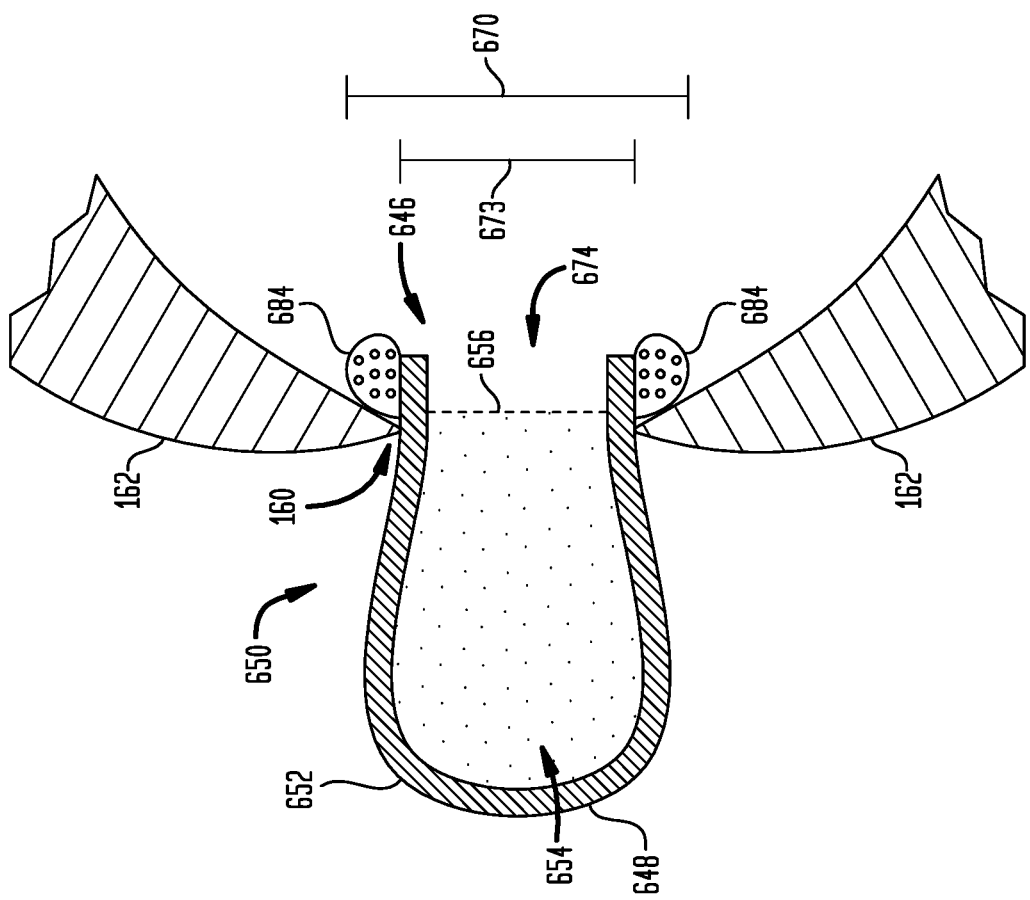
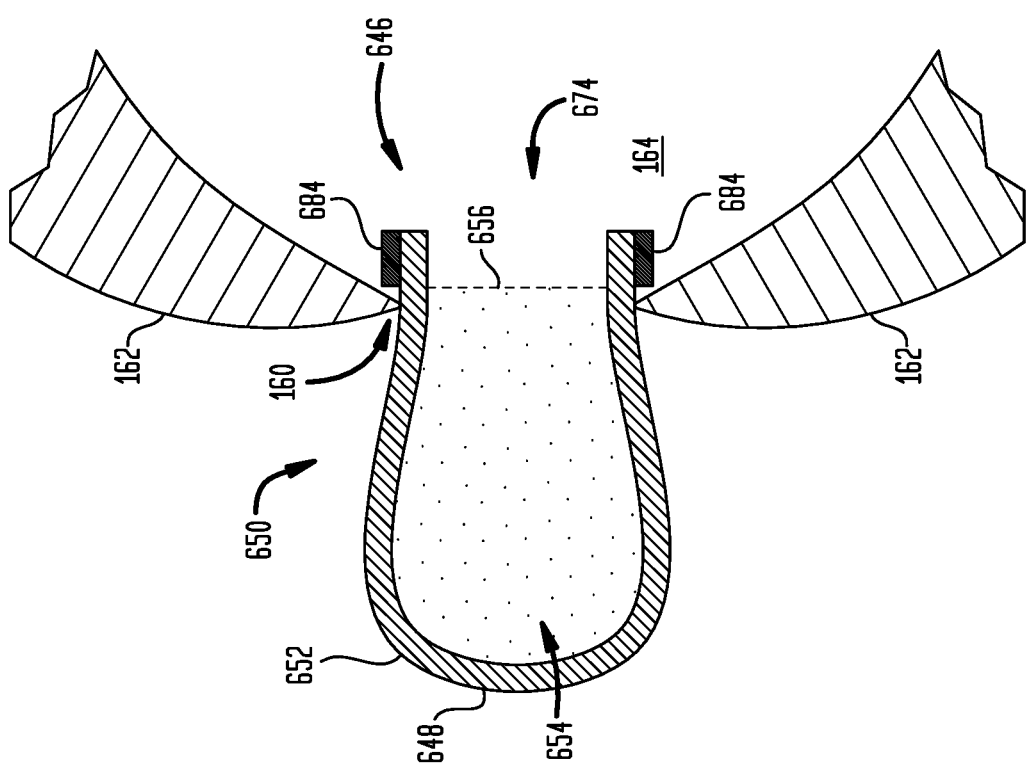

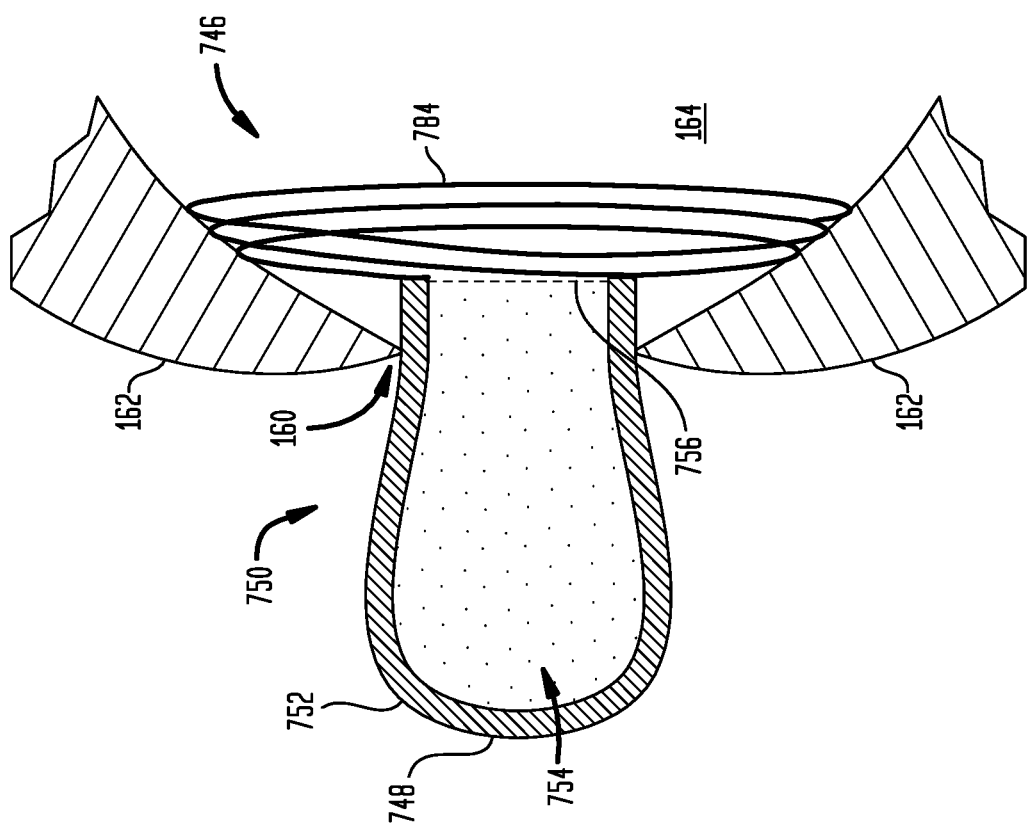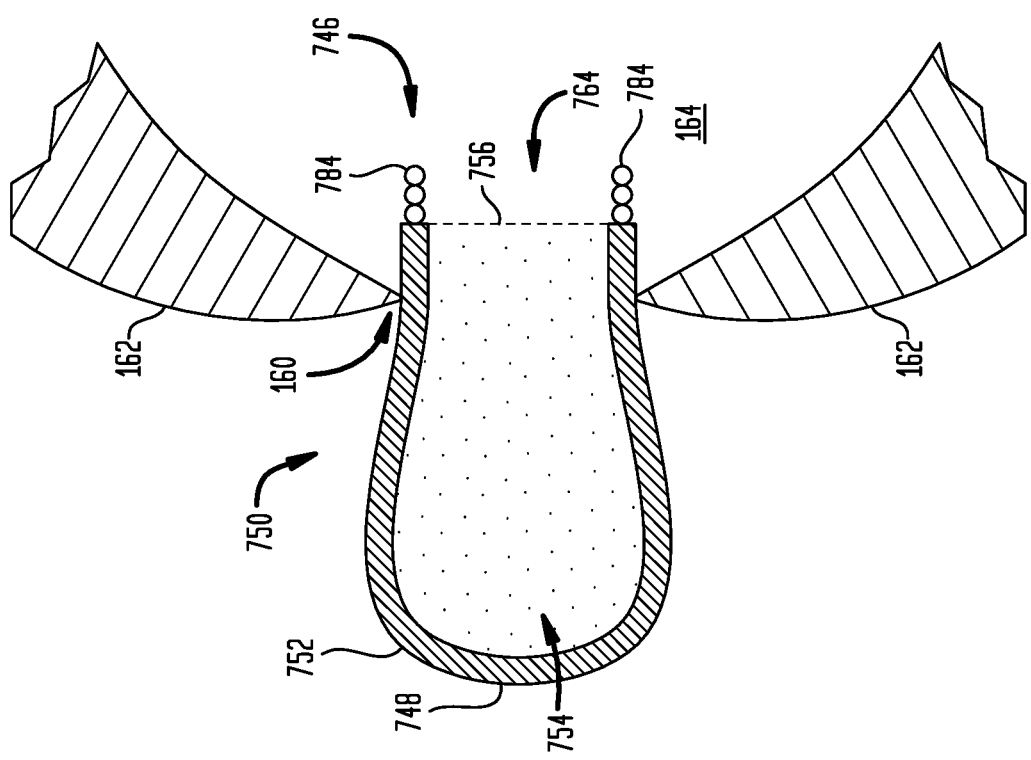

INNER EAR PLUG

BACKGROUND

Field of the Invention

The present invention relates generally to inner ear drug delivery.

Related Art

Hearing loss, for example, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain. In certain cases, hearing loss, in particular sensorineural hearing loss, is associated with (e.g., caused by) diseases of the inner ear.

SUMMARY

In one aspect of the invention, a securable inner ear drug delivery plug is provided. The securable drug delivery plug comprises: a body for insertion into an opening in an inner ear of a recipient; at least one passive drug delivery mechanism configured to deliver one or more drugs directly into the inner ear; and one or more anchoring features that are configured to secure the body within the inner ear opening.

In another aspect of the present invention, a method is provided. The method comprises: inserting a drug delivery plug into an opening in an inner ear of a recipient, wherein the drug delivery plug extends through the opening; securing, with one or more anchoring features formed in the drug delivery plug, the drug delivery plug within the opening; and passively releasing a drug from the drug delivery plug directly into the inner ear.

BRIEF DESCRIPTION OF THE DRAWINGS

Embodiments of the present invention are described herein in conjunction with the accompanying drawings, in which:

FIGS. 5A and 5B are cross-sectional views of another securable inner ear drug delivery plug in accordance with embodiments presented herein;

FIGS. 6A and 6B are cross-sectional views of another securable inner ear drug delivery plug in accordance with embodiments presented herein;

FIGS. 7A and 7B are cross-sectional views of another securable inner ear drug delivery plug in accordance with embodiments presented herein;

DETAILED DESCRIPTION

Diseases of the inner ear include disorders that affect an individual's auditory system and/or vestibular system. These inner ear diseases frequently result in, or contribute to, a variety of medical problems, such as hearing loss, vertigo, tinnitus, Ménière's disease, etc. It may be desirable to address these medical problems with localized/targeted delivery of substances (e.g., biological or bioactive), chemicals, pharmaceutical agents, nanoparticles, ions, DNA/RNA molecules, proteins, peptides, RNAi, etc. (generally and collectively referred to herein as "treatment substances" or simply "drugs") that are designed to treat/address the underlying inner ear disease. Drugs may also be delivered to prevent infection, to facilitate healing, to preserve hearing, to prevent fibrosis, etc. As such, as used herein, "drugs" or "treatment substances" include, but are not limited to, bioactive substances, chemicals, or other deliverable substances used for therapeutic, prophylactic, diagnostic, or other purposes, including active pharmaceutical ingredients (APIs) (e.g., antibiotics, anti-inflammatories, antimicrobials, etc.).

Despite a rapidly expanding pipeline of potential cochlear therapeutics, the inner ear remains a challenging organ for targeted drug delivery in a safe and efficacious manner. For example, conventional drug delivery techniques often result in only a limited amount of the drug actually reaching the inner ear, therefore necessitating increases in applied drug dosages which, in turn, increase the side effects of the respective drugs. Localized drug delivery to the inner ear via one or more inner ear openings (e.g., the round window, the oval window, a cochleostomy, etc.) ameliorates these issues. As such, embodiments of the present invention are directed to a securable inner drug delivery plug or stopper that is configured to be inserted into, and secured (retained) within, an opening of the inner ear of an individual and configured to deliver drugs directly into the inner ear. An individual into which a securable inner drug delivery plug is implanted is referred to herein as a "recipient" of the securable inner drug delivery plug.

Securable inner ear drug delivery plugs in accordance with embodiments of the present invention may be used alone or combination with any partially or fully-implantable hearing prosthesis, such as a bone conduction device, a mechanical stimulator, an auditory brain implant, a cochlear implant, etc. However, merely for ease of illustration, securable inner ear drug delivery plugs are primarily described and shown separate from any partially or fully-implantable hearing prostheses.

Figure 1A:
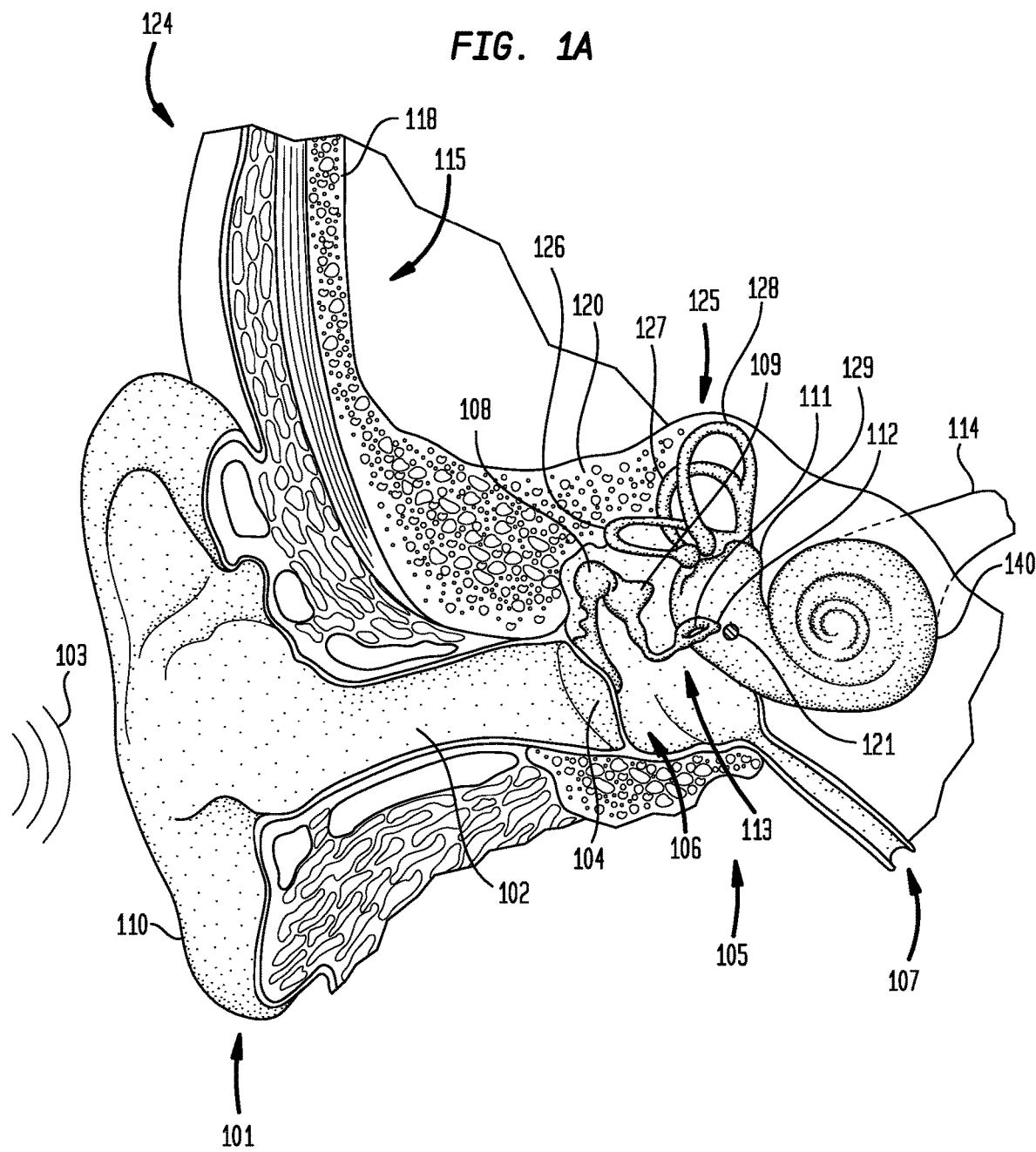
FIG. 1A is a schematic diagram illustrating the anatomy of a recipient at a location in which a securable inner ear drug delivery plug in accordance with embodiments presented herein may be implanted.

Before describing illustrative embodiments of the securable inner drug delivery plug, a brief description of the human anatomy of a recipient's ear is first provided with reference to FIG. 1A.

As shown in FIG. 1A, a recipient's ear comprises an outer ear 101, a middle ear 105 and an inner ear 107. In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112, which is adjacent round window 121, through the bones of the middle ear 105. The bones of the middle ear 105 comprise the malleus 108, the incus 109 and the stapes 111, collectively referred to as the ossicles 106. The ossicles 106 are positioned in the middle ear cavity 113 and serve to filter and amplify the sound wave 103, causing oval window 112 to articulate (vibrate) in response to the vibration of tympanic membrane 104. This vibration of the oval window 112 sets up waves of fluid motion of the perilymph within the cochlea 140, which forms part of the inner ear 107. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound The human skull is formed from a number of different bones that support various anatomical features. Illustrated in FIG. 1A is the temporal bone 115 which is situated at the side and base of the recipient's skull 124. For ease of reference, the temporal bone 115 is referred to herein as having a superior portion 118 and a mastoid portion 120. The superior portion 118 comprises the section of the temporal bone 115 that extends superior to the auricle 110. That is, the superior portion 118 is the section of the temporal bone 115 that forms the side surface of the skull. The mastoid portion 120, referred to herein simply as the mastoid 120, is positioned inferior to the superior portion 118. The mastoid 120 is the section of the temporal bone 115 that surrounds the middle ear 105.

As shown in FIG. 1A, semicircular canals 125 are three half-circular, interconnected tubes located adjacent cochlea 140. The semicircular canals 125 also form part of the inner ear 107 and are in fluid communication with the cochlea 140 via the vestibule 129. The three semicircular canals comprise the horizontal semicircular canal 126, the posterior semicircular canal 127, and the superior semicircular canal 128. The canals 126, 127 and 128 are aligned approximately orthogonally to one another. Specifically, when the individual is in an upright position, the horizontal canal 126 is aligned roughly horizontally in the head, while the superior 128 and posterior canals 127 are aligned roughly at a 45 degree angle to a vertical through the center of the individual's head.

Each semicircular canal is filled with a fluid called endolymph and contains a motion sensor with tiny hairs (not shown) whose ends are embedded in a gelatinous structure called the cupula (also not shown). As the orientation of the skull changes, the endolymph is forced into different sections of the canals. The hairs detect when the endolymph passes thereby, and a signal is then sent to the brain. Using these hair cells, horizontal canal 126 detects horizontal head movements, while the superior 128 and posterior 127 canals detect vertical head movements.

As noted, embodiments of the present invention are directed to a drug delivery plug for insertion into an opening in a recipient's inner ear. The inner ear openings into which the drug delivery plug may include, for example, a natural opening, such as the oval window 112 or the round window 121 which are each sealed by a membrane, or a surgically created opening (e.g., a cochleostomy or a surgically created opening in one of the semicircular canals). As described further below, in addition to comprising at least one passive drug delivery mechanism, the drug delivery plug also includes one or more anchoring features that are configured to secure (retain) the drug delivery plug within the inner ear opening. As described further below, the one or more anchoring features are configured to substantially prevent withdrawal or removal of the plug without surgical intervention (e.g., surgical removal of the plug). As such, drug delivery plugs in accordance with embodiments of the present invention are referred to as securable inner ear drug delivery plugs, indicating that the plugs are: (1) configured to deliver one or more drugs directly to (i.e., straight into) the recipient's inner ear, and (2) configured to be anchored or otherwise substantially permanently secured within the inner ear opening. The drug delivery mechanisms presented herein are "passive" because the mechanisms do not utilize any active components, such as a pump, to deliver the drugs to the recipient.

Figure 1B:
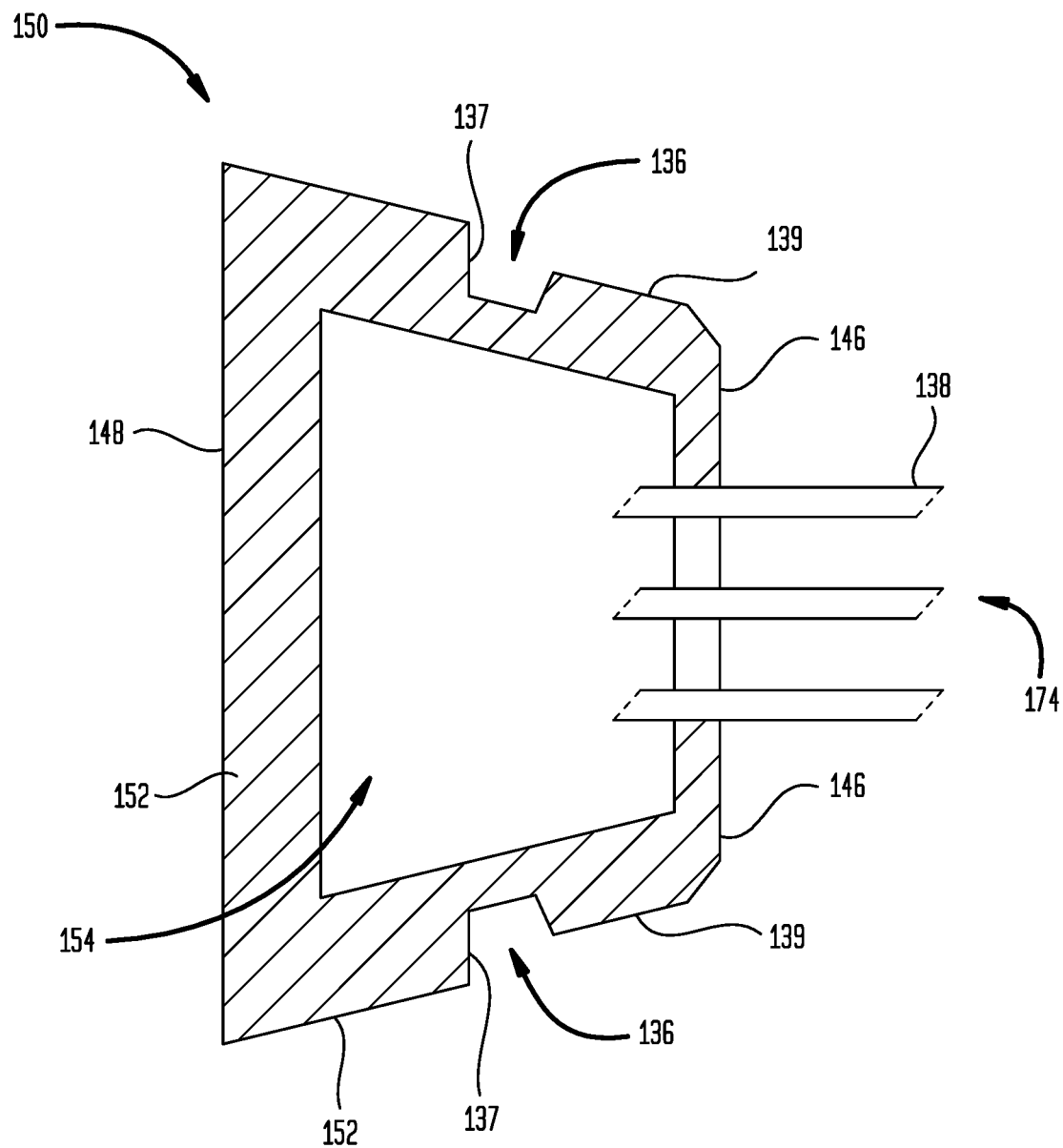
FIGS. 1B and 1C are cross-sectional views of a securable inner ear drug delivery plug in accordance with embodiments presented herein.
Figure 1C:
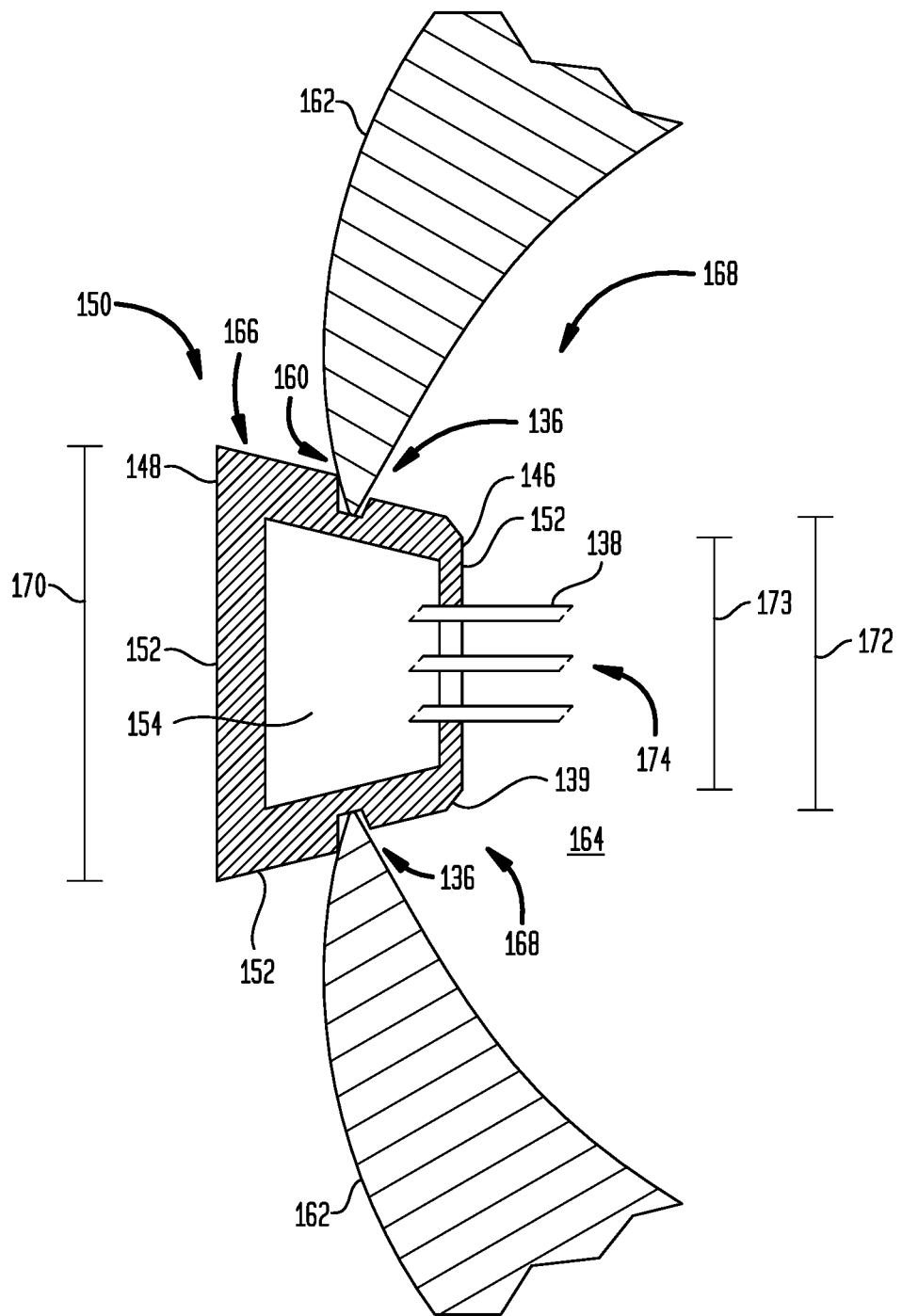

FIGS. 1B and 1C are cross-sectional views of a securable inner ear drug delivery plug 150 that may be inserted and secured in, for example, the oval window 112, the round window 121, a cochleostomy or other surgically created opening, etc. in the inner ear. For ease of description and unless specified otherwise, the oval window 112, the round window 121, a cochleostomy or other surgically created opening, or any other opening into which a securable inner ear drug delivery plug may be inserted and secured are collectively and generally referred herein as "inner ear openings."

FIG. 1B illustrates the securable inner ear drug delivery plug 150 separate from an inner ear opening, while FIG. 1C illustrates the securable inner ear drug delivery plug 150 positioned in an inner ear opening 160. As shown, the securable inner ear drug delivery plug 150 comprises an outer body 152 that surrounds/defines an interior region 154 in which one or more drugs are disposed. In the example of FIGS. 1B and 1C, the interior region 154 is a reservoir of one or more liquid drugs. That is, the outer body 152 is a substantially non-permeable element forming a container that holds the one or more liquid drugs.

In the embodiment of FIGS. 1A and 1B, the securable inner ear drug delivery plug 150 has a proximal end 148 and a distal end 146. The distal end 146 is configured to be inserted through an opening 160 within the structure 162 of a recipient's inner ear (i.e., cochlea or semicircular canals) 164, while the proximal end 148 is configured to remain outside (external to) the inner ear. That is, when fully implanted/inserted, a first portion 166 of the securable inner ear drug delivery plug 150 is disposed/positioned outside of the inner ear 164, while a second portion 168 of the securable inner ear drug delivery plug 250 is disposed inside (within) the inner ear 164 (i.e., the securable inner ear drug delivery plug 250 is configured to be partially inserted into the inner ear 164). As used herein, a securable inner ear drug delivery plug, such as plug 150, is fully inserted/implanted when the distal end 146 of the plug is located within the inner ear 164, and the outer body 152 substantially fills the opening 160.

As noted, securable inner ear drug delivery plugs in accordance with embodiments of the present invention, such as plug 150, include a passive drug delivery mechanism that delivers one or more drugs directly into the inner ear. In the embodiment of FIGS. 1A and 1B, the passive drug delivery mechanism 174 is provided by the reservoir 154 and one or more drug delivery tubes/conduits 138. As shown in FIG. 1C, when the securable inner ear drug delivery plug 150 is positioned within the opening 160, the drug delivery tubes 138 each extend from the reservoir 154 through the outer body 152 into the inner ear 164. As such, a drug within the reservoir 154 may exit the reservoir and enter the inner ear via the drug delivery tubes 138 (i.e., the drug delivery tube provide a pathway for the one or more drugs to exit the reservoir and enter the inner ear). The drug delivery mechanism 174 is considered "passive" because it does not utilize any active components, such as a pump, to deliver the drugs to the recipient.

It is to be appreciated that a liquid drug disposed in the reservoir 154 may exit the reservoir and enter the inner ear via the delivery tubes 138 as a result of various actions and/or forces. For example, in one embodiment, a drug exits the delivery tubes 138 as a result of capillary forces. In certain such embodiments, to control the release of the liquid drug, the delivery tubes 138 may include an inner coating or surfactant that alters the resistance of the inner surface to the flow of the liquid drug. For example, the inner surface of the delivery tubes 138 may include an inner coating or surfactant that changes the surface hydrophobicity to alter the rate of drug release. In an alternative embodiment, a similar result could be achieved by adjusting the viscosity of the liquid drug with one or more additives.

In another embodiment, a liquid drug disposed in the reservoir 154 may exit the reservoir and enter the inner ear via the delivery tubes 138 due to, at least in part, compression forces. For example, in one embodiment the outer body 152 is resiliently flexible so as to be at least partially compressible, for example, during insertion through the opening 160. The compressibility of the outer body 152 may facilitate the insertion of the plug 150 through the opening 160 (i.e., temporarily reduce the outer dimension of the plug 150 during insertion), but this compression may also facilitate delivery of the drug via the drug delivery tubes 138. More specifically, compression of the outer body 152 after the distal end 146 has passed through the opening 160 may, in turn, compress the reservoir 154 so as to force a portion of the drug within the reservoir through the delivery tubes 138. After the initial compression, the outer body 152 may return to its initial shape and any of the drug remaining in the reservoir 154 may exit the reservoir 154 via, for example, capillary forces as described above. In these embodiments, the outer body 152 may each be formed from a polymeric mated al, such as, for example, Polydimethylsiloxane (PDMS) or another type of silicone.

In certain examples, a distal end of one or more of the delivery tubes 138 may be sealed with a permeable or bioresorbable membrane so that a time-frame for delivery of the drug may be controlled.

It is also to be appreciated that, in alternative embodiments, a securable inner ear drug delivery plug may have different numbers of drug delivery tubes. It is also to be appreciated that the drug delivery tubes 138 may have a variety of different arrangements. For example, in one embodiment, the delivery tubes 138 may contain or be coated with a compound to prevent fibrotic growth and/or with various types of drugs. The delivery tubes 138 may be formed from the same or different material as the outer body 152.

It is to be appreciated that the reservoir 154 may include multiple different types of drugs. That is, in accordance with embodiments of the present invention, multiple different drugs could be disposed in reservoir 154 for delivery to a recipient. It is also to be appreciated that the inner region 154 may include more than one reservoir each associated with one or more of the drug delivery tubes 138.

As noted, the securable inner ear drug delivery plug 150 may be inserted into opening 160, which may be any natural opening (e.g., the oval window 112 or the round window 121) or a surgically created (artificial) opening in the inner ear. However, the arrangement of FIGS. 1A and 1B may be particularly advantageous when used with the oval window 112 or the round window 121. In particular, the oval window 112 and the round window 121 are each naturally sealed by a membrane. Therefore, if a plug is to be inserted into the oval window 112 or the round window 121, the membrane must first be opened. In the embodiments of FIGS. 1B and 1C, the drug delivery tubes 138 have sufficient longitudinal rigidity and/or a suitable distal configuration so as to pierce/perforate the membrane so that the securable inner ear drug delivery plug 150 may directly inserted through (i.e., pushed through) the membrane. That is, the securable inner ear drug delivery plug 150 is self-piercing so that the plug can be inserted into the recipient without the need to pre-pierce the membrane with a surgical instrument.

As noted, securable inner ear drug delivery plugs in accordance with embodiments of the present invention, such as plug 150, include one or more anchoring features that are configured to anchor or otherwise substantially permanently secure the plug within the inner ear opening (i.e., prevent withdrawal or removal of the plug without surgical intervention). In the embodiment of FIGS. 1A and 1B, the one or more anchoring features comprise an annular depression or groove 136 disposed around a portion of the outer body 152. The groove 136 is formed by a stop surface 137 and a distal flange 139 and is configured to mate with the inner ear structures surrounding the opening 160.

More specifically, the distal flange 139 is disposed at the distal end 146 of the securable inner ear drug delivery plug 150 and is configured such that the distal end 146 has an outer dimension (e.g., diameter) 172 that is larger than the inner dimension 173 (e.g., diameter) of the opening 160. The distal flange 139 is formed from a resiliently flexible material such that, when the securable inner ear drug delivery plug 150 is inserted into the opening 160, the distal flange 139 is configured to be compressed so as to pass through the opening. However, due to the resilient/elastic properties of the distal flange 139, the distal flange 139 is configured to return to the pre-insertion (non-compressed) configuration after passing through the opening 160. That is, the distal flange 139 "springs" outward or away from the outer body 152 to return to the pre-insertion configuration once the distal flange 139 passes through the opening 160.

As shown in FIG. 1C, after the distal flange 139 passes through the opening 160, the stop surface 137 will contact an outer surface of the inner ear structure 162 so as to prevent additional forward (distal) movement of the securable inner ear drug delivery plug 150. When the stop surface 137 contacts the outer surface of the inner ear, the inner ear structures surrounding the opening 160 become locked within the groove 136 where additional forward movement is prevented by the stop surface 137, and rearward (proximal) movement is prevented by the distal flange 139. As a result, the securable inner ear drug delivery plug 150 is secured within the opening 160.

In certain embodiments, the groove 136 may include one or more features that operate to further secure the securable inner ear drug delivery plug 150. For example, the groove 136 may be textured to increase friction forces between the inner ear structures surrounding the opening 160 and the surface of the groove. In addition or alternatively, one or more biocompatible adhesives may be disposed in the groove 136.

FIGS. 1B and 1C have been described with reference to outer body 152 formed from a biocompatible polymer material. It is to be appreciated that the outer body 152 could also be formed from, for example, a biocompatible metal (e.g., titanium), ceramic, and/or a combination of these or other materials.

FIGS. 1B and 1C also illustrate that the outer body 152 has a general frustoconical or tapered shape where the outer dimension (e.g., width, diameter, etc.) of the outer body 152 generally increases from the distal end 146 to the proximal end 148 (i.e., an outer dimension 170 of the proximal end 248 is larger than the outer dimension 172 of the distal end 146). The frustoconical or tapered shape may also facilitate sealing of the opening 260 by applying an outward force on the inner ear structures adjacent to the opening 160. Although FIGS. 1A and 1B illustrate that the outer body 252 has a frustoconical shape, it is to be appreciated that securable inner ear drug delivery plugs in accordance with embodiments of the present invention may have other shapes.

In the embodiments of the FIGS. 1B and 1C, the securable inner ear drug delivery plug 150 is configured to fill and seal the opening 160 so as to prevent the egress of inner ear fluid through the opening (i.e., around the plug). However, it is to be appreciated that the plug 150, or other plugs described herein, may partially seal the opening 160. In such embodiments, the securable inner ear drug delivery plugs may be used with one or more additional sealing elements and/or drugs that control the growth of tissue to seal the opening. In one example, one or more portions of the securable inner ear drug delivery plug 150 may be pre-loaded (doped) with a drug that promotes tissue growth around the plug. After implantation, the drug may then elute from the one or more portions of the securable inner ear drug delivery plug 150.

In certain embodiments, a securable inner ear drug delivery plug in accordance with embodiments presented herein, such as plug 150, may be re-filled after implantation. In one example, a securable inner ear drug delivery plug in accordance with embodiments presented herein may be re-filled via a syringe injection through the outer body or through a syringe port.

Figure 2:
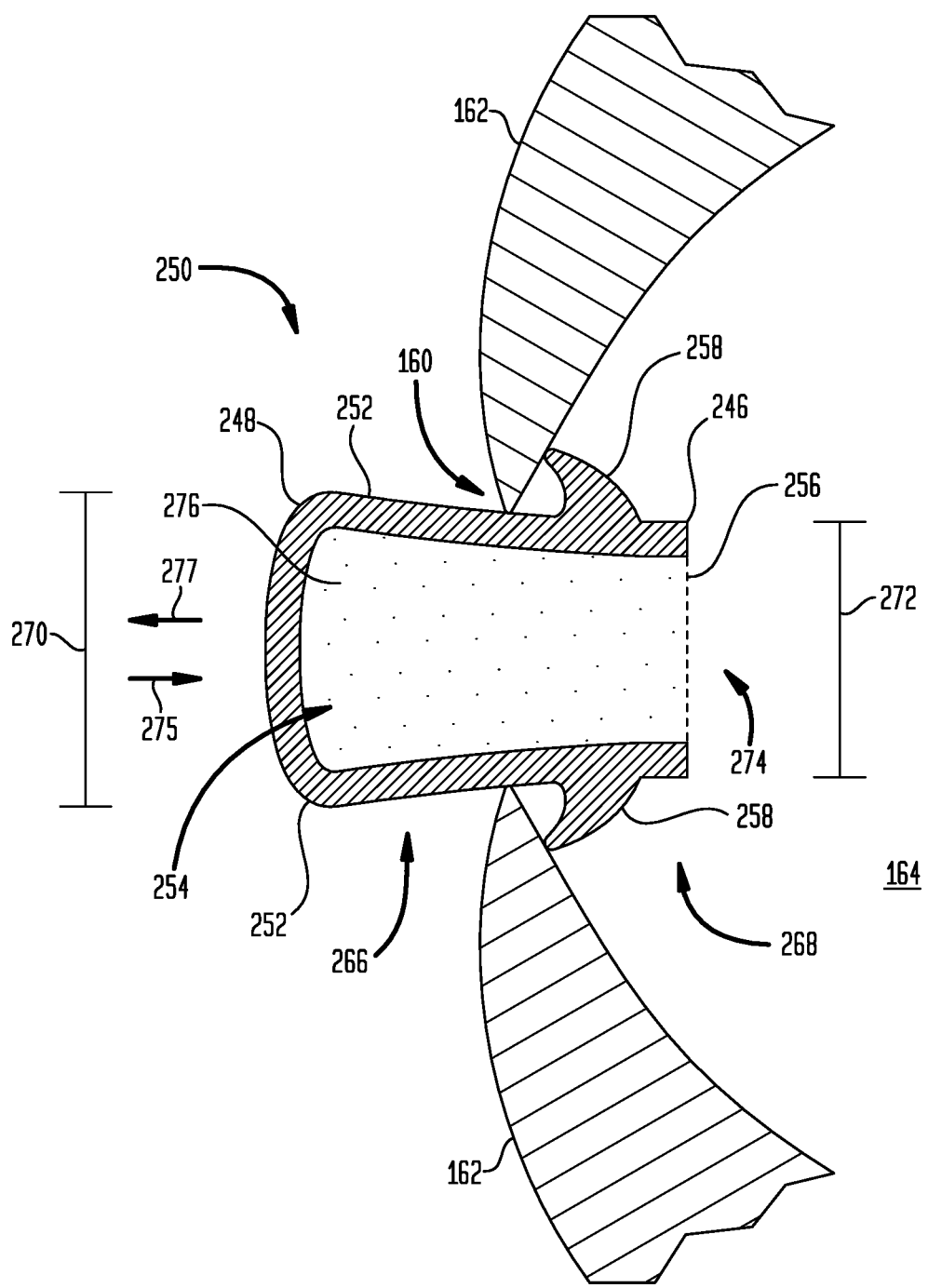
FIG. 2 is a cross-sectional view of another securable inner ear drug delivery plug in accordance with embodiments presented herein.

FIG. 2 is a cross-sectional view of another securable inner ear drug delivery plug 250 in accordance with embodiments of the present invention. Securable inner ear drug delivery plug 250 comprises an outer body 252 defining an interior region 254. In this embodiment, a drug-eluting member 276 is disposed within interior region 254. Also shown in FIG. 2 is a permeable membrane 256 and one or more unidirectional (one-way) securement tabs 258. In the embodiment of FIG. 2, the securable inner ear drug delivery plug 250 has a proximal end 248 and a distal end 244. The distal end 246 is configured to be inserted through an opening 160 within the structure 162 of a recipient's inner ear (i.e., cochlea or semicircular canals) 164, while the proximal end 246 is configured to remain outside (external to) the inner ear. That is, when fully implanted, a first portion 266 of the securable inner ear drug delivery plug 250 is disposed/positioned outside of the inner ear 164, while a second portion 268 of the securable inner ear drug delivery plug 250 is disposed inside (within) the inner ear 164 (i.e., the securable inner ear drug delivery plug 250 is configured to be partially inserted into the inner ear 164).

In certain examples, the outer body 252 is sized and shaped to control/limit a depth of insertion of the securable inner ear drug delivery plug 250 into the inner ear 164. For example, the outer body 252 may have a general frustoconical or tapered shape where the outer dimension (e.g., width, diameter, etc.) of the outer body 252 generally increases from the distal end 246 to the proximal end 248 (i.e., an outer dimension 270 of the proximal end 248 is larger than an outer dimension 272 of the distal end 246). The increase in the outer dimension of the outer body 252 between the distal end and the proximal end enables the first portion 266 of the securable inner ear drug delivery plug 250 to be inserted through the opening 160, while preventing the second portion 268 from passing through the opening 160 (i.e., the frustoconical or tapered shape for outer body 252 limit the depth of insertion of the plug). In addition to limiting the insertion depth, the frustonical or tapered shape may also facilitate sealing of the opening 160 by applying an outward force on the inner ear structures adjacent to the opening 160. Although FIG. 2 illustrates that the outer body 252 has a frustoconical shape, it is to be appreciated that securable inner ear drug delivery plugs in accordance with embodiments of the present invention may have other shapes to control/limit a depth of insertion of the plug.

As noted, securable inner ear drug delivery plugs in accordance with embodiments of the present invention, such as plug 250, include: (1) a passive drug delivery mechanism that delivers drugs directly into the inner ear, and (2) one or more anchoring features that are configured to anchor or otherwise substantially permanently secure the plug within the inner ear opening. In the embodiment of FIG. 2, the passive drug delivery mechanism 274 is provided by the permeable membrane 256 and the drug-eluting member 276 disposed within the interior region 254. The one or more anchoring features are formed by unidirectional securement tabs 258.

Referring first to the passive drug delivery mechanism 274, the drug-eluting member 276 is a polymeric element that is pre-loaded (doped) with one or more drugs (i.e., drug delivery drug-eluting member 276 releasably carries one or more drugs). In operation, the drugs within the drug-eluting member 276 elute from the drug-eluting member 276 and enter the inner ear 164 via (through) the permeable membrane 256. In particular, the outer body 252 is substantially impermeable to the drugs and substantially surrounds portions of the drug-eluting member 276 not adjacent to the permeable membrane 256. As such, the drugs with the drug-eluting member 276 are directed through the permeable membrane 256. In certain embodiments, elution of the drug within the drug-eluting member 276 may be caused or activated by, for example, contact with the inner ear fluid, a temperature increase to the recipient's body temperature, etc. Outer body 252 and drug-eluting member 276 may each be formed from the same or different polymeric materials, such as, for example, Polydimethylsiloxane (PDMS).

As noted, FIG. 2 illustrates the use of a drug-eluting member 276 disposed within an interior region 254. However, it is to be appreciated that in other embodiments the interior region 254 may define a reservoir that is directly filled with a liquid drug or a solid drug configured to change forms when placed in contact with the inner ear fluid (via the permeable membrane). In such embodiments, the drug exits the reservoir and enters the inner ear 164 via the permeable membrane 256. That is, the permeable membrane 256 seals the reservoir during insertion of the plug, but that allows release of the drugs after insertion of the plug. For example, the permeable membrane 156 may be configured to change form after implantation so as to release the drug. The permeable membrane 156 may change from a closed/sealed form to a permeable form as a result of contact with fluid (e.g., the inner ear fluid) or in response to a temperature change induced by the recipient's body. In one example, the permeable membrane 256 is a "semi-permeable" membrane that, instead of changing form upon liquid contact, it relies on diffusion and gradient effects. In further embodiments, a protective film may be provided over the permeable membrane 256 and removed just before or during implantation (preferably together with a drug loaded fluid with high viscosity).

It is to be appreciated that the drug eluting member 276 (or a reservoir) may include multiple different types of drugs. That is, in accordance with embodiments of the present invention, multiple different drugs could be disposed in interior region 254 for delivery to a recipient.

Referring next to the one or more anchoring features, the unidirectional securement tabs 258 are elements that allow insertion of the plug (i.e., allow movement in a distal direction illustrated by arrow 275), but that resist or prevent withdrawal of the plug (i.e., resist movement in a proximal direction illustrated by arrow 277). In particular, the unidirectional securement tabs 258 extend out from a surface of the outer body 252 and have an initial shape and/or orientation. However, as shown in FIG. 2B, the unidirectional securement tabs 258 are configured to be compressed as the unidirectional securement tabs 258 pass through the opening 160. As such, the inner ear structure(s) surrounding the opening 160 force the unidirectional securement tabs 258 to bend backwards (i.e., in the proximal direction 277) toward the proximal end 248. However, due to the resilient/elastic properties of the unidirectional securement tabs 258, the unidirectional securement tabs are configured to return to the pre-insertion configuration after passing through the opening 160. That is, the unidirectional securement tabs 258 "spring" outward or away from the outer body 252 to return to the pre-insertion configuration once the unidirectional securement tabs 258 pass the opening 160.

When the unidirectional securement tabs 258 pass the opening 160 and return to their pre-insertion configuration, the surgeon may place a tensile force on (i.e., pull) the securable inner ear drug delivery plug 250 in the proximal direction 277. Application of the tensile force causes the unidirectional securement tabs 258 to be forced against surfaces of the inner ear adjacent to the opening 160. In turn, the surfaces place forces on the unidirectional securement tabs 258 in the distal direction 275. Although the unidirectional securement tabs 258 are configured to bend backwards (i.e., in the proximal direction), the unidirectional securement tabs 258 are configured such that they do not bend in the forward (distal) direction (e.g., have rigidity in the distal direction). In other words, the unidirectional securement tabs 258 engage an inner surface of the inner ear). As such, the engagement of the unidirectional securement tabs 258 with the surfaces around the opening 160 prevents movement of the securable inner ear drug delivery plug 250 out of the inner ear 164 the opening 160 (i.e., secure the securable inner ear drug delivery plug 250 within the opening 160). The unidirectional securement tabs 258 in accordance with embodiments of the present invention may be formed from, for example, silicone, polyimide or PEEK, or a resilient or elastic metal.

In the embodiment of FIG. 2, the outer body 252 is resiliently flexible so as to be at least partially compressible during insertion through the opening 160. The compressibility of the outer body 252 may facilitate the insertion of the securement tabs 258 through the opening 160 (i.e., temporarily reduce the outer dimension of the plug 250 during insertion). However, the compressibility of the outer body 252 may also facilitate delivery of the drug within interior region 254 directly into the inner ear 164. More specifically, compression of the outer body 252 after the distal end 246 has passed through the opening 160 may compress the drug-eluting member 276 so as to force drugs through the permeable membrane 256.

FIG. 2 has being described with reference to outer body 252 formed from a biocompatible polymer material. It is to be appreciated that the outer body 252 could also be formed from, for example, a biocompatible metal (e.g., titanium), a ceramic, and/or combinations of these or other materials.

FIG. 2 illustrates an example in which the unidirectional securement tabs 258 are a plurality of discrete (separate) elements disposed at different locations around the outer body 252. In alternative embodiments, the securable drug delivery plug 250 may include a single unidirectional securement tab. A single unidirectional securement tab may comprise a continuous flange/collar extending around the outer body 252.

Figure 3:
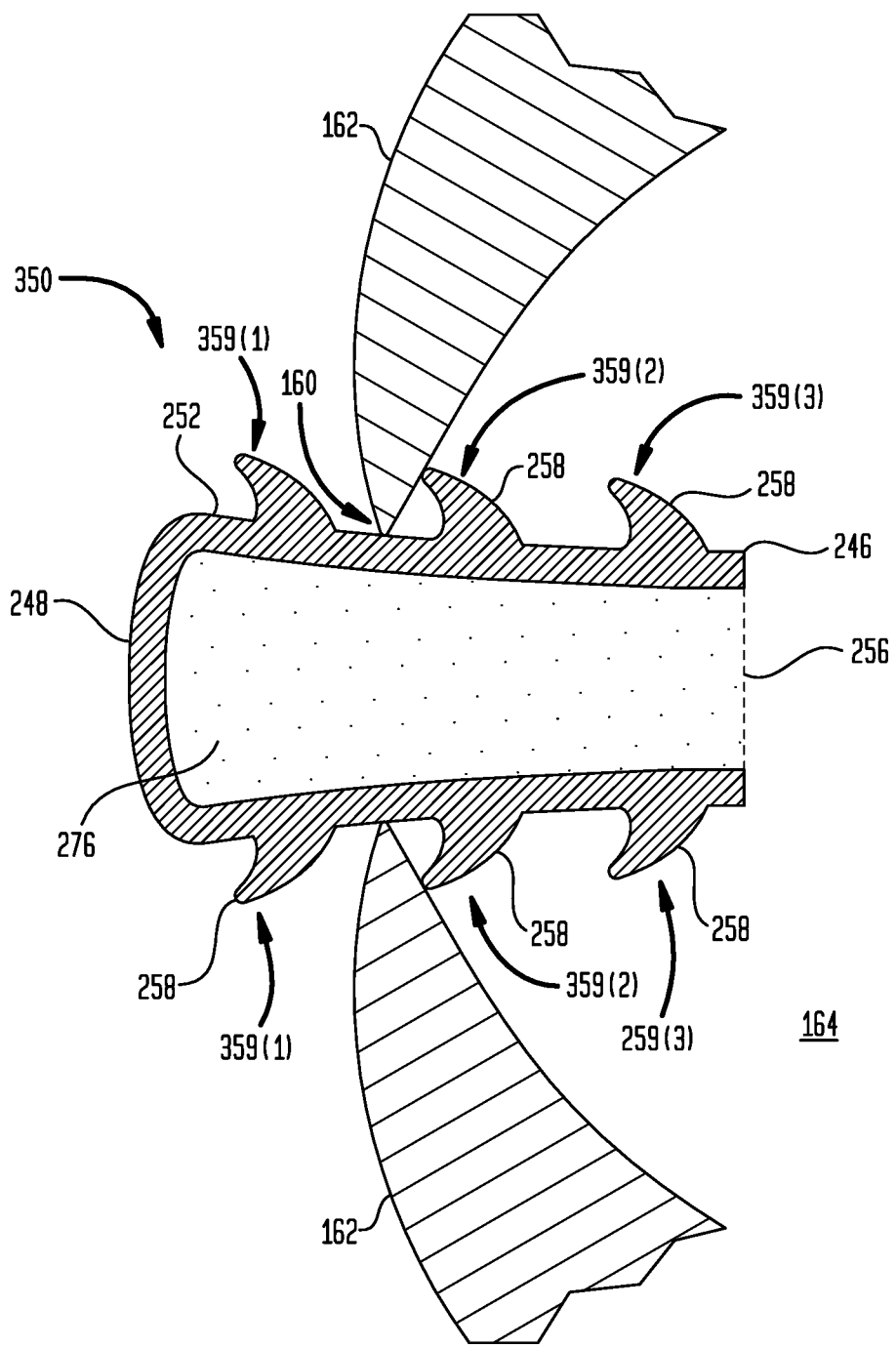
FIG. 3 is a cross-sectional view of another securable inner ear drug delivery plug in accordance with embodiments presented herein.

FIG. 3 is a cross-sectional diagram illustrating another embodiment of the present invention. In FIG. 3, a securable inner ear drug delivery plug 350 has a similar arrangement to that shown in FIG. 2, including an outer body 252, a drug-eluting member 276, and a permeable membrane 256. However, in this embodiment of FIG. 3, the outer body 252 includes a plurality of longitudinally-spaced sets or groups 359(1), 359(2), and 359(3) of unidirectional securement tabs 258. In general, the three sets 359(1), 359(2), and 359(3) of unidirectional securement tabs 258 each include one or more unidirectional securement tabs 258 and collectively provide a surgeon with the ability to select one of several different insertion depths for the securable inner ear drug delivery plug 350. That is, any one of the sets 359(1), 359(2), and 359(3) can be used to secure the securable inner ear drug delivery plug 350 within the opening 160, thereby accommodating variations in the anatomy of different recipients.

Figure 4:
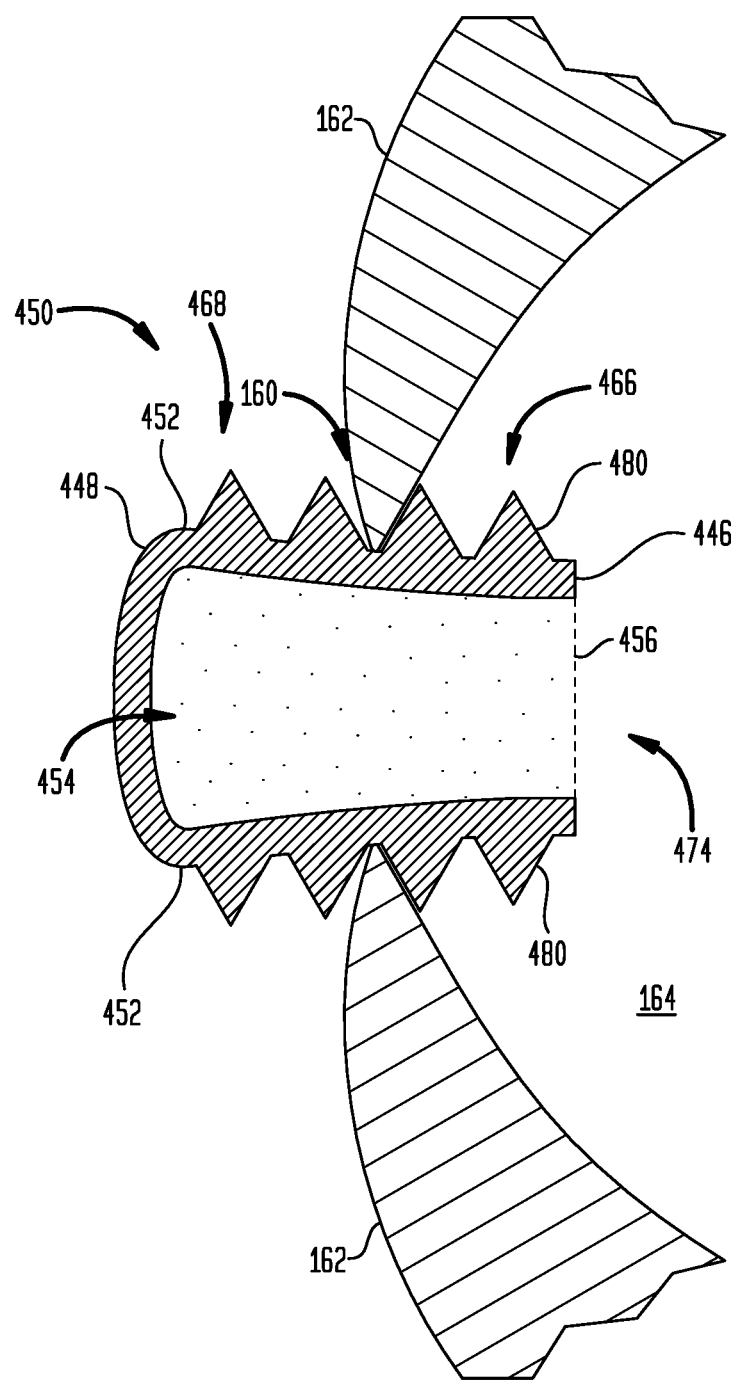
FIG. 4 is a cross-sectional view of another securable inner ear drug delivery plug in accordance with embodiments presented herein.

FIG. 4 is a cross-sectional view of a securable inner ear drug delivery plug 450 in accordance with embodiments of the present invention. Securable inner ear drug delivery plug 450 comprises an outer body 452 defining an interior region 454 in which one or more drugs are disposed. In the example of FIG. 4, the interior region 454 is a reservoir of one or more drugs. However, it is to be appreciated that the interior region 454 could, in alternative arrangements, include a drug-eluting member. Disposed at a distal end 446 of the of the securable inner ear drug delivery plug 450 is a permeable membrane 456 that seals the reservoir 454 during insertion of the plug, but that allows release of the drugs after insertion of the plug.

In the embodiment of FIG. 4, the securable inner ear drug delivery plug 450 is configured to be partially inserted into the inner ear 164. That is, the distal end 446 is configured to be inserted through the opening 160, while a proximal end 448 is configured to remain outside the inner ear (i.e., a first portion 466 of the securable inner ear drug delivery plug 250 is positioned outside of the inner ear 164, while a second portion 468 of the securable inner ear drug delivery plug 450 is disposed inside the inner ear 164).

As shown, the outer body 452 is sized and shaped to limit an insertion depth of the securable inner ear drug delivery plug 450. That is, the outer body 452 has a general frustoconical or tapered shape where the outer dimension of the outer body 452 generally increases from the distal end 446 to the proximal end 448. Although FIG. 4 illustrates that the outer body 452 has a frustoconical shape, it is to be appreciated that the securable inner ear drug delivery plug 450 may have other shapes.

In the embodiment of FIG. 4, the securable inner ear drug delivery plug 450 includes a passive drug delivery mechanism 474 formed by the permeable membrane 456 and the reservoir 454. In operation, the drug(s) within the reservoir 454 exit the reservoir and enter the inner ear 164 via (through) the permeable membrane 456. In particular, the outer body 452 is substantially impermeable to the drugs so that the drugs are directed through the permeable membrane 456.

Securable inner ear drug delivery plug 450 includes one or more anchoring features in the form of screw threads 480 disposed around the outer body 452. As such, the outer body 452 comprises a threaded body (shank) that is configured to be inserted (e.g., screwed) into the opening 160. The screw threads 480 interact with (engage) the walls surrounding the opening 160 to retain the securable inner ear drug delivery plug 450 within the opening.

In the example of FIG. 4, the outer body 452 and the screw threads 480 are formed from a resiliently flexible material (e.g., silicone) so that the body and screw threads are partially compressed when placed in contact with the walls surrounding the opening 160 (i.e., when screwed into the opening). The compression of the screw threads further secures the securable inner ear drug delivery plug 450 within the opening 160, but also operates to seal the opening 160 to prevent leakage of inner ear fluid past the plug.

Although FIG. 4 illustrates an embodiment in which the outer body 452 and the screw threads 480 are formed from a resiliently flexible material, it is to be appreciated that, in other embodiments, the outer body 452 and the screw threads 480 may be formed from different materials. For example, the outer body 452 and the screw threads 480 may be formed from a substantially rigid material (e.g., titanium) that is configured to integrate with the walls surrounding the opening 160. In such embodiments, the integration of the screw threads with the walls surrounding opening 160 secures the securable inner ear drug delivery plug within the opening, but also seals the opening to prevent leakage of inner ear fluid past the plug.

FIGS. 5A and 5B are cross-sectional views of a securable inner ear drug delivery plug 550 in accordance with embodiments of the present invention. FIG. 5A illustrates the securable inner ear drug delivery plug 550 immediately after insertion into an inner ear opening 160, while FIG. 5B illustrates the securable inner ear drug delivery plug 550 at a subsequent time (i.e., some time after the initial insertion).

Securable inner ear drug delivery plug 550 comprises an outer body 552 defining an interior region 554 in which one or more drugs are disposed. In the example of FIGS. 5A and 5B, the interior region 554 is a reservoir of one or more drugs. However, it is to be appreciated that the interior region 554 could, in alternative arrangements, include a drug-eluting member.

In the embodiment of FIGS. 5A and 5B, the securable inner ear drug delivery plug 550 is configured to be partially inserted into the inner ear 164. That is, the distal end 546 is configured to be inserted through the opening 160, while a proximal end 548 is configured to remain outside the inner ear. As shown, the outer body 552 is sized and shaped to limit an insertion depth of the securable inner ear drug delivery plug 550. That is, the outer body 552 has a general frustoconical or tapered shape where the outer dimension of the outer body 552 generally increases from the distal end 546 to the proximal end 548. Although FIGS. 5A and 5B illustrate that the outer body 552 has a frustoconical shape, it is to be appreciated that the securable inner ear drug delivery plug 550 may have other shapes.

Securable inner ear drug delivery plug 550 includes one or more anchoring features in the form of an expandable component 582. As shown in FIG. 5B, the expandable component 582 is a component that is configured to expand (e.g., swell) when exposed to the recipient's inner ear fluid, such as the perilymph or endolymph. That is, after insertion into the inner ear 164, the expandable component 582 is allowed to take on the inner ear fluid (i.e., the fluid penetrates the matrix and the material swells) so as to reach a post-insertion outer dimension 570 that is larger than an inner dimension 573 of the opening 160. The larger outer dimension 570 of the expandable component 582 prevents movement of the securable inner ear drug delivery plug 550 (i.e., the expandable component 582 engages an inner surface within the inner ear to prevent withdrawal of the plug). In certain examples, the expandable component 582, when in an expanded (enlarged) configuration, the expandable component is configured to exert a force on the inner ear structures surrounding the opening 160 so as to further lock the securable inner ear drug delivery plug 550 within the opening.

The expandable component 582 may be formed from different materials and have different arrangements. In one embodiment, expandable component 582 is a polymeric material that is configured to swell (i.e., expand) when exposed to a recipient's bodily fluid. In another embodiment, the expandable component 582 is a dried and compressed sponge that is configured to absorb the inner ear fluid after insertion.

FIGS. 5A and 5B illustrate a specific arrangement in which a non-permeable film 586 is a portion of the expandable component 582. In these embodiments, the non-permeable film 586 is located between the expandable component 582 and the inner surface of the recipient's inner ear structure adjacent to opening 160. As such, when the expandable component 582 expands, the non-permeable film 586 may be compressed between the expandable component 582 and the inner surface of the recipient's inner ear structure to reduce/avoid leakage of inner ear fluid through the opening 160.

In the embodiment of FIGS. 5A and 5B, the securable inner ear drug delivery plug 550 includes a passive drug delivery mechanism 574 formed by the reservoir 554 and the expandable component 582. In operation, the drug(s) within the reservoir 554 exit the reservoir and enter the inner ear 164 via (through) the expandable component 582. In an alternative arrangement, one or more drug delivery tubes may extend through the expandable component 582 to bypass the expandable component 582 and facilitate delivery of the drug(s) within the reservoir 554.

FIGS. 6A and 6B are cross-sectional views of a securable inner ear drug delivery plug 650 that is similar to the plug 550 shown in FIGS. 5A and 5B. FIG. 6A illustrates the securable inner ear drug delivery plug 650 immediately after insertion into an inner ear opening 160, while FIG. 6B illustrates the securable inner ear drug delivery plug 650 at a subsequent time (i.e., some time after the initial insertion).

Securable inner ear drug delivery plug 650 comprises an outer body 652 defining an interior region 654 in which one or more drugs are disposed. In the example of FIGS. 6A and 6B, the interior region 654 is a reservoir of one or more drugs. However, it is to be appreciated that the interior region 654 could, in alternative arrangements, include a drug-eluting member.

In the embodiment of FIGS. 6A and 6B, the securable inner ear drug delivery plug 650 is configured to be partially inserted into the inner ear 164. That is, the distal end 646 is configured to be inserted through the opening 160, while a proximal end 648 is configured to remain outside the inner ear. As shown, the outer body 652 is sized and shaped to limit an insertion depth of the securable inner ear drug delivery plug 650. That is, the outer body 652 has a general frustoconical or tapered shape where the outer dimension of the outer body 652 generally increases from the distal end 646 to the proximal end 648. Although FIGS. 6A and 6B illustrate that the outer body 652 has a frustoconical shape, it is to be appreciated that the securable inner ear drug delivery plug 650 may have other shapes.

Securable inner ear drug delivery plug 650 includes one or more anchoring features in the form of two or more expandable components 682. As shown in FIG. 6B, the expandable components 682 are configured to expand (e.g., swell) when exposed to the recipient's inner ear fluid. That is, the expandable components 682 takes on the inner ear fluid (i.e., the fluid penetrates the matrix and the material swells) so that the distal end 646 reaches a post-insertion outer dimension 670 that is larger than an inner dimension 673 of the opening 160. The larger outer dimension 670 of the distal end 646 prevents movement of the securable inner ear drug delivery plug 650. In certain examples, the expandable components 682, when in an expanded (enlarged) configuration, are configured to exert a force on the inner ear structures surrounding the opening 160 so as to further lock the securable inner ear drug delivery plug 650 within the opening.

The expandable components 682 may be formed from a number of different materials and may have a variety of different arrangements. In one embodiment, the expandable components 682 are formed from a polymeric material that is configured to swell (i.e., expand) when exposed to a recipient's bodily fluid. In another embodiment, the expandable components 682 are dried and compressed sponges that are configured to absorb the inner ear fluid after insertion.

In the embodiment of FIGS. 6A and 6B, the securable inner ear drug delivery plug 650 includes a passive drug delivery mechanism 674 formed by the reservoir 654 and a permeable membrane 656 disposed at a distal end of the reservoir. In operation, the drug(s) within the reservoir 654 exit the reservoir and enter the inner ear 164 via (through) the permeable membrane 656.

FIGS. 7A and 7B are cross-sectional views of another securable inner ear drug delivery plug 750 that also includes an expandable component. FIG. 7A illustrates the securable inner ear drug delivery plug 750 immediately after insertion into an inner ear opening 160, while FIG. 7B illustrates the securable inner ear drug delivery plug 750 at a subsequent time (i.e., some time after the initial insertion).

Securable inner ear drug delivery plug 750 comprises an outer body 752 defining an interior region 754 in which one or more drugs are disposed. In the example of FIGS. 7A and 7B, the interior region 754 is a reservoir of one or more drugs. However, it is to be appreciated that the interior region 754 could, in alternative arrangements, include a drug-eluting member.

In the embodiment of FIGS. 7A and 7B, the securable inner ear drug delivery plug 750 is configured to be partially inserted into the inner ear 164. That is, the distal end 746 is configured to be inserted through the opening 160, while a proximal end 748 is configured to remain outside the inner ear. As shown, the outer body 752 is sized and shaped to limit an insertion depth of the securable inner ear drug delivery plug 750. That is, the outer body 752 has a general frustoconical or tapered shape where the outer dimension of the outer body 752 generally increases from the distal end 746 to the proximal end 748. Although FIGS. 7A and 7B illustrate that the outer body 752 has a frustoconical shape, it is to be appreciated that securable inner ear drug delivery plug 750 may have other shapes.

Securable inner ear drug delivery plug 750 includes one or more anchoring features in the form of an expandable component 782. The expandable component 782 is a memory material element (e.g., a nitinol wire) that is configured to expand when heated to the recipient's body temperature. That is, as shown in FIG. 7B, the expandable component 782, when heated to the recipient's body temperature, expands to so as to have an outer dimension 770 that is larger than an inner dimension of the opening 160, thereby prevent movement of the securable inner ear drug delivery plug 750. In certain examples, the expandable component 782, when in an expanded (enlarged) configuration, is configured to exert a force on the inner ear structures surrounding the opening 160 so as to further lock the securable inner ear drug delivery plug 750 within the opening.

In the embodiment of FIGS. 7A and 7B, the securable inner ear drug delivery plug 750 includes a passive drug delivery mechanism 774 formed by the reservoir 754 and a permeable membrane 756 disposed at a distal end of the reservoir. In operation, the drug(s) within the reservoir 754 exit the reservoir and enter the inner ear 164 via (through) the permeable membrane 756.

Collectively, FIGS. 5A-7B illustrate securable inner ear drug delivery plugs that include one or more anchoring structures in the form of components that are configured expand after insertion of the plug into an opening in the inner ear. These expandable anchoring features are positioned at the distal end of the associated plug and are configured to prevent removal/withdrawal of the plug through the inner ear opening.

Figure 8A:
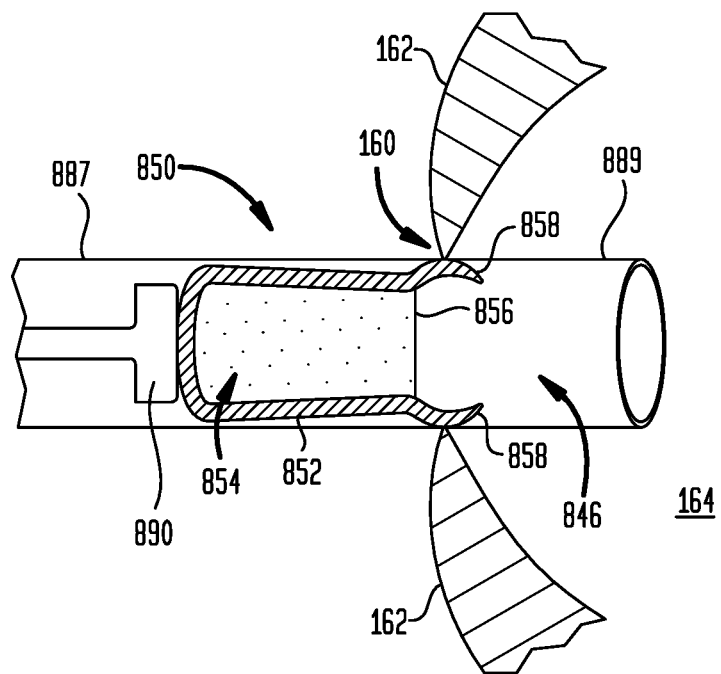
FIGS. 8A and 8B are cross-sectional views of another securable inner ear drug delivery plug in accordance with embodiments presented herein.
Figure 8B:
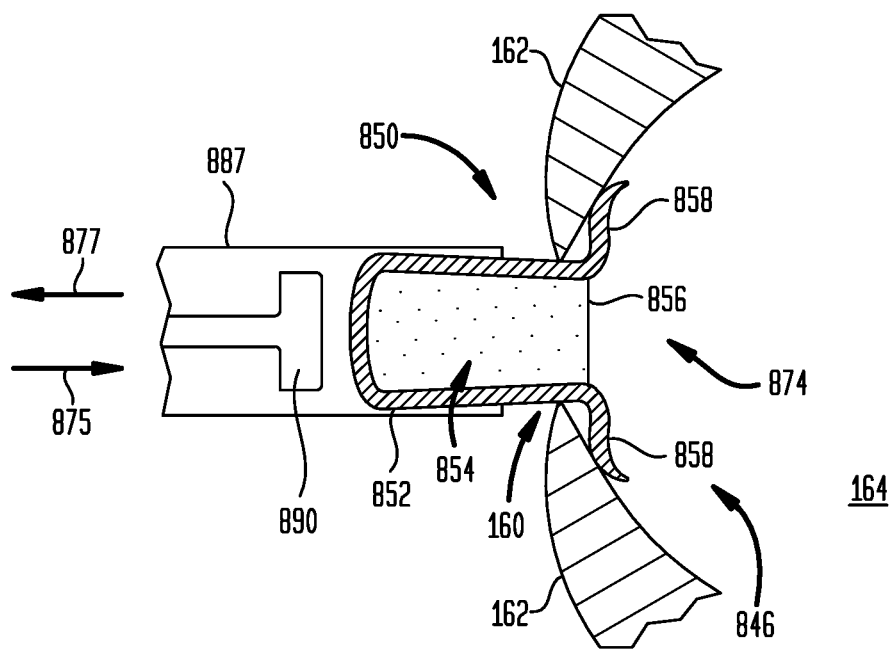

FIGS. 8A and 8B are cross-sectional views illustrating another securable inner ear drug delivery plug 850, and a mechanism for delivery of the plug, in accordance with embodiments of the present invention. FIG. 8A illustrates the securable inner ear drug delivery plug 850 prior to insertion into an inner ear opening 160, while FIG. 8B illustrates the securable inner ear drug delivery plug 850 immediately after insertion into the inner ear opening 160.

Similar to arrangements described above, securable inner ear drug delivery plug 850 comprises an outer body 852 defining an interior region 854 that forms a reservoir for one or more drugs. Disposed at the distal end 846 of the outer body 852 is a permeable membrane 856 and one or more tabs or flanges 858.

As shown in FIG. 8A, the securable inner ear drug delivery plug 850 is initially positioned within a plug delivery tube 887. The delivery tube 887 is sized so as to fit into an inner ear opening 160, as well as to compress the outer body 852 and the flanges 858. During insertion, a distal end 889 of the delivery tube 887 is inserted through the opening 160. A plunger 890 is then used to push the securable inner ear drug delivery plug 850 in a forward/distal direction 875 to force at least the distal end 846 of the securable inner ear drug delivery plug 850 out the distal end 889 of the delivery tube 887. When the distal end 846 of the securable inner ear drug delivery plug 850 exits the distal end 889 of the delivery tube 887, the flanges 858 decompress to a configuration with an outer dimension that is larger than an inner dimension of the opening 160, thereby so as to thereby prevent proximal movement of the securable inner ear drug delivery plug 850 (i.e., movement in direction 877). The flanges 858 may be silicone components, metal springs, or any other element that can be compressed during insertion via the delivery tube 887.

Once at least the distal end 846 of the securable inner ear drug delivery plug 850 exits the distal end 889 of the delivery tube 887, the delivery tube is withdrawn from the opening 160 (i.e., moved in a proximal direction 877). The delivery tube 887 and plunger 890 may then be removed from the recipient.

As noted, the outer body 852 is also compressed when located in the delivery tube 887. As such, removal of the delivery tube 887 allows the outer body 852 to de-compress so as to substantially fill the opening 160.

In the embodiment of FIGS. 8A and 8B, the securable inner ear drug delivery plug 850 includes a passive drug delivery mechanism 874 formed by the reservoir 854 and the permeable membrane 856 disposed at a distal end of the reservoir. In operation, the drug(s) within the reservoir 854 exit the reservoir and enter the inner ear 164 via (through) the permeable membrane 856.

Figure 9B:
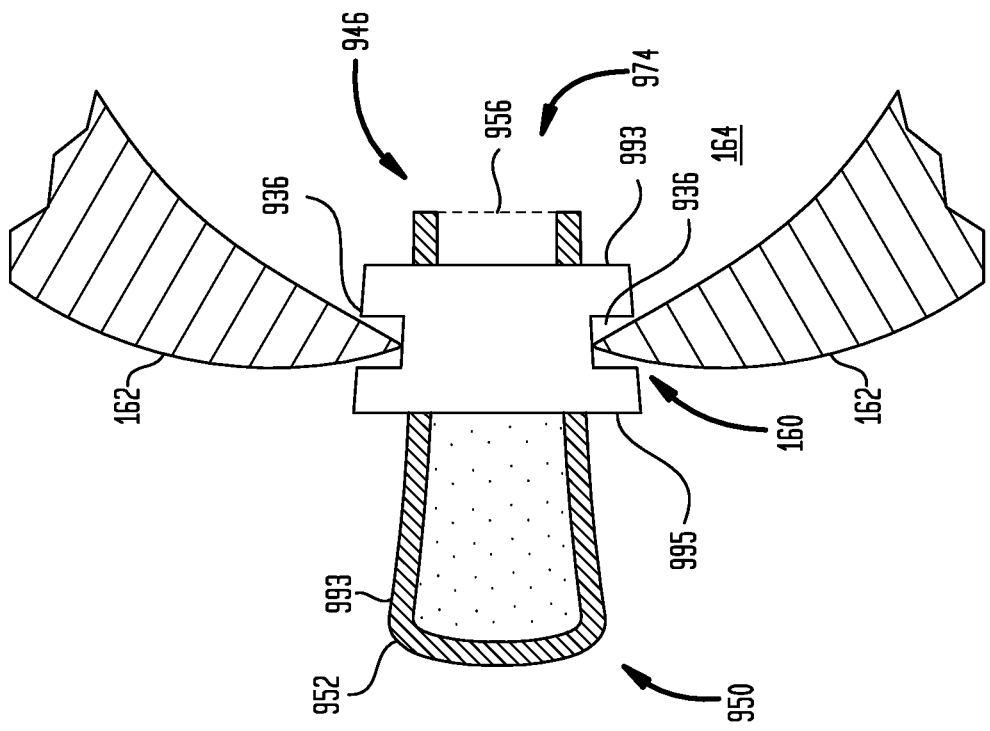
FIGS. 9A and 9B are cross-sectional views of another securable inner ear drug delivery plug in accordance with embodiments presented herein.
Figure 9A:
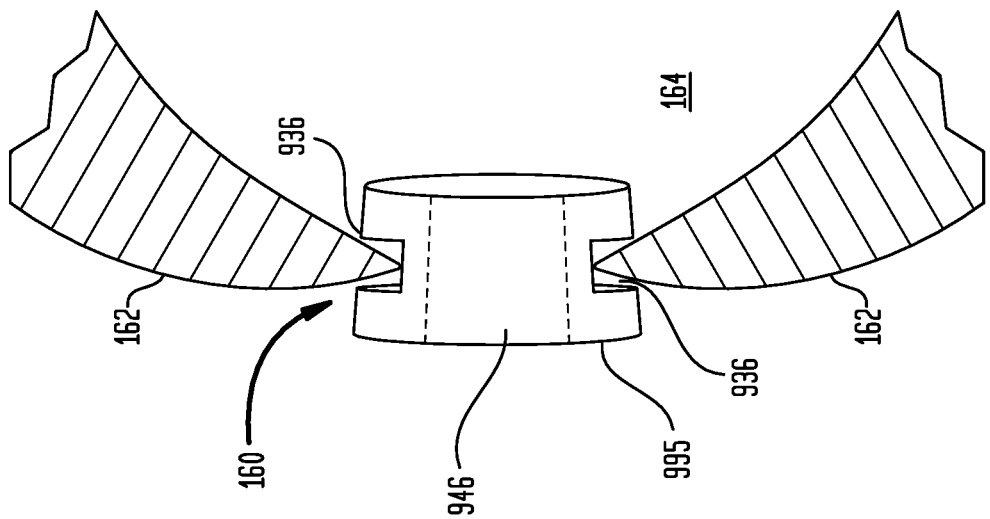

FIGS. 9A and 9B are cross-sectional views of a two-stage or two-part securable inner ear drug delivery plug 950 in accordance with embodiments of present invention. In particular, the securable inner ear drug delivery plug 950 comprises a main member 993 and a compressible grommet 993 formed, for example, from a biocompatible rubber or other compressible material.

The main member 993 comprises an outer body 952 defining an interior region 954 that forms a reservoir for one or more drugs. Disposed at the distal end 946 of the outer body 952 is a permeable membrane 956. The reservoir 954 and the permeable membrane 956 disposed at the distal end of the outer body 952 operate as a drug delivery mechanism 974.

As shown in FIG. 9A, the compressible grommet 995 includes an annular depression or groove 936 disposed around an outer surface of the grommet. When the grommet 995 is disposed in the opening 160, the groove 936 is configured to mate with the inner ear structures surrounding the opening 160.

The grommet 995 has a lumen 996 extending there through. As shown in FIG. 9B, the main member 993 is configured to be inserted into the lumen 996 and is configured to exert an outward force on the compressible grommet 995 to secure the main member 993 within the lumen 996 and, accordingly, within the opening 160. That is, in the embodiment of FIGS. 9A and 9B, the outer body 952 is formed from a material that is substantially rigid relative to the grommet 995 so that the grommet is compressed between the inner ear structures surrounding the opening 160 and the outer body 952. Compression of the grommet 995 operates to secure the main member 993 within the lumen 966 and, accordingly, the opening 160 (i.e., the compressible grommet 995 is an anchoring feature). In addition, compression of the grommet 995 operates to substantially seal the opening 160 and, accordingly, prevent leakage of inner ear fluid around the plug 950.

In certain examples, an interface may be provided between the main member 993 and the grommet 995. This interface may be, for example, a screw interface, an interlocking interface, etc. An interface may allow for changing the reservoir if, for example, more or another drug is needed. Also, this interlocking interface can later be used for anchoring an intra-cochlear stimulating assembly, as needed.

Figure 10:
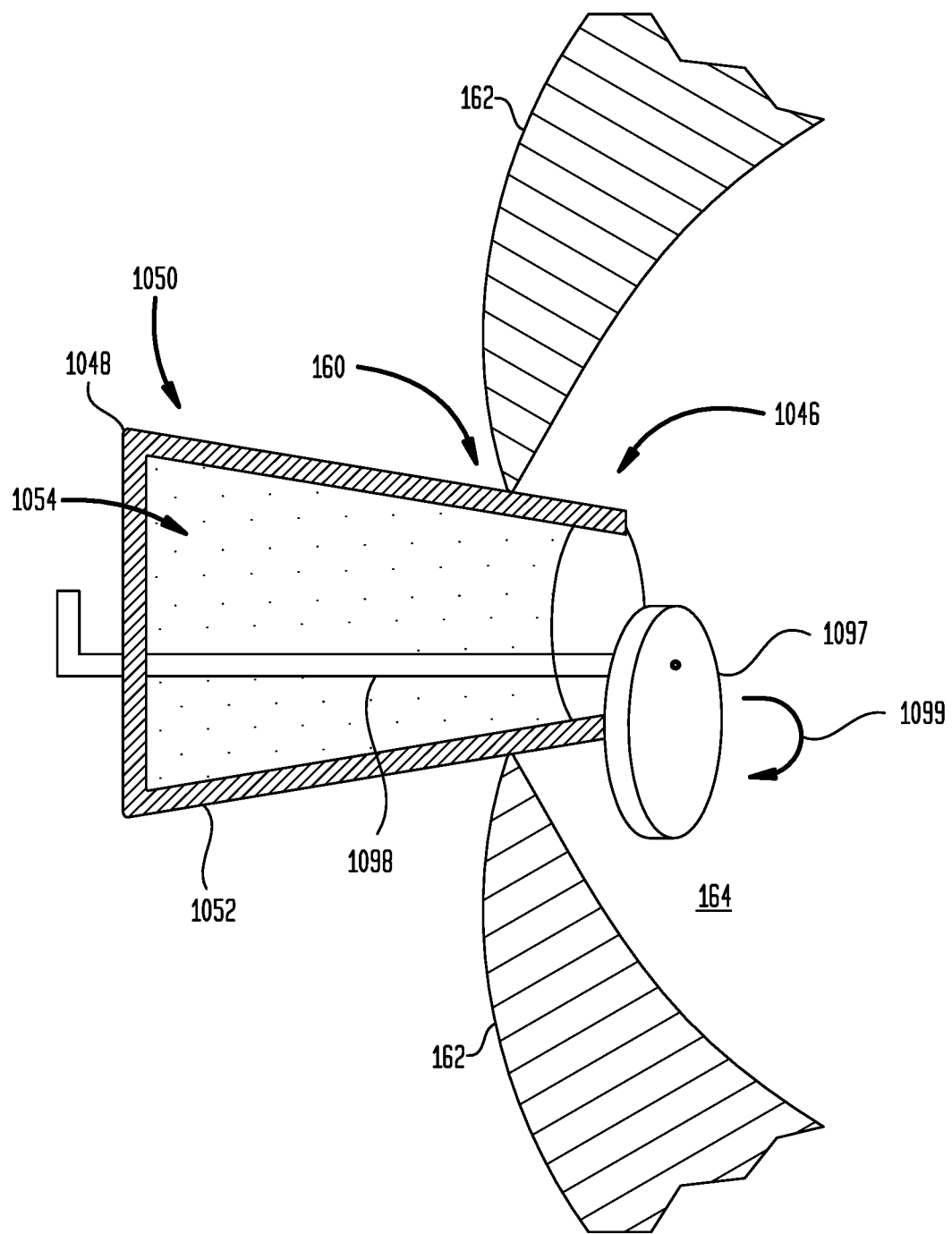
FIG. 10 is a cross-sectional view of another securable inner ear drug delivery plug in accordance with embodiments presented herein.

FIG. 10 is a cross-sectional view of another securable inner ear drug delivery plug 1050 in accordance with embodiments of present invention. The securable inner ear drug delivery plug 1050 comprises an outer body 1052 defining an interior region 1054 that forms a reservoir for one or more drugs. Disposed at the distal end 1046 of the outer body 1052 is a rotatable disk 1097 that is mechanically attached to a rotation arm 1098. The rotation arm 1098 extends longitudinally from the rotatable disk 1097 through the proximal end 1048 of the securable inner ear drug delivery plug 1050 so as to be accessible and actuatable/manipulated by a surgeon.

As shown in FIG. 10, the securable inner ear drug delivery plug 1050 is configured to be partially inserted into the inner ear 164. That is, the distal end 1046 is configured to be inserted through the opening 160, while a proximal end 1048 is configured to remain outside the inner ear. As shown, the outer body 1052 is sized and shaped to limit an insertion depth of the securable inner ear drug delivery plug 1050 (e.g., the outer body 1052 has a general frustoconical or tapered shape).

Once the securable inner ear drug delivery plug 1050 is fully inserted into the opening 160, the rotation arm 1098 may be actuated so that the disk 1097 rotates (e.g., asymmetrically) in the general direction shown by arrow 1099. After the rotation, the rotatable disk 1097 is positioned adjacent to the inner ear structures surrounding the opening 160 so as to prevent movement of the securable inner ear drug delivery plug 1050 in a proximal direction.

In the specific example of FIG. 10, the rotatable disk 1097 is also a cover for the reservoir 1054. As such, the reservoir 1054 and the rotatable disk 1097 collectively operate as a drug delivery mechanism 1074 for the securable inner ear drug delivery plug 1050. However, it is to be appreciated that the rotatable disk 1097 may not cover the reservoir 1054 in other embodiments. For example, in alternative embodiments, the rotatable disk 1097 may only cover a portion of the distal end of the reservoir 1054. In such embodiments, the securable inner ear drug delivery plug 1050 may include one or more other mechanisms (e.g., a permeable membrane) that operate to control the delivery of drugs from the reservoir 1054 to the inner ear (i.e., other elements forming part of the drug delivery mechanism). It is also to be appreciated that the use of one rotatable disk 1097 is illustrative and that other embodiments may use multiple rotatable disks to secure a plug within an inner ear opening.

It is to be appreciated that arrangements other than that shown in FIG. 10 are possible. For example, the reservoir may be secured by, for example, prongs/flanges (as described above), while the rotatable disk operates to provide drug delivery in that it can be partially opened (administering a lower dose), or fully opened (giving a high dose). In other words, the arrangement of FIG. 10 could include other anchoring features and the rotatable disk is used primarily for drug delivery.

The above description illustrates various embodiments for securable inner ear drug delivery plugs in accordance with embodiments of the present invention. It is to be appreciated that the above described embodiments are not mutually exclusive and that the various embodiments can be combined in various manners and arrangements. That is, the above described drug delivery mechanisms and anchoring features may be combined and used in a number of different combinations. It is also to be appreciated that other embodiments for drug delivery mechanisms and anchor features are within the scope of the present invention. For example, embodiments may include expandable components in the form of prongs/flanges (e.g., deflatable/inflatable flanges) that may be deployed after a securable inner ear drug delivery plug is inserted into an inner ear opening.

Furthermore, it is to be appreciated that auxiliary securement mechanisms in addition to the one or more anchoring features may be used in certain embodiments. These auxiliary securement mechanisms may include a biocompatible bonding agent (e.g., adhesive) applied to one or more portions of a plug. The bone agent may be, for example, an ionomeric bone cement or a poly methyl methacrylate (PMMA) bone cement. In other embodiments, the bonding agent may be any biocompatible adhesive now known or later developed. In certain embodiments, the bonding agent may be configured to be resorbed by the recipient's tissue/bone after fibrotic encapsulation by the recipient's tissue/bone.

In further embodiments, a securable inner ear drug delivery plug may be formed from a material configured to harden when exposed to ultra-violet (UV) light. In such embodiments, the UV light may be delivered after the securable inner ear drug delivery plug is positioned in an inner ear opening.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A securable inner ear drug delivery plug, comprising:
a body for insertion into an opening in an inner ear of a recipient, wherein the body has an elongate frustoconical shape;
at least one passive drug delivery mechanism configured to deliver one or more drugs directly into the inner ear via the body; and
screw threads extending along an outer surface of the body and configured to be screwed into the inner ear opening to mechanically mate with a surface of an inner ear structure surrounding the inner ear opening to fluidically seal the inner ear opening to prevent egress of inner ear fluid through the inner ear opening past the screw threads.

2. The securable inner ear drug delivery plug of claim 1, wherein the screw threads comprise a material configured to be compressed between the outer surface of the body and the inner ear structure surrounding the opening in the inner ear of the recipient.

3. The securable inner ear drug delivery plug of claim 1, wherein the screw threads comprise a rigid material configured to integrate with the inner ear structure surrounding the opening in the inner ear of the recipient.

4. The securable inner ear drug delivery plug of claim 1, further comprising:
a drug-eluting member disposed in the body.

5. The securable inner ear drug delivery plug of claim 1, wherein the body defines a plurality of reservoirs each configured to have at least one drug positioned therein.

6. The securable inner ear drug delivery plug of claim 1, wherein the body defines a reservoir for one or more drugs.

7. The securable inner ear drug delivery plug of claim 6, further comprising:
a membrane positioned at a distal end of the reservoir, wherein the membrane is configured to seal the reservoir during insertion of the body into the opening and to allow release of the one or more drugs after insertion of the body into the opening.

8. The securable inner ear drug delivery plug of claim 6, further comprising:
one or more drug delivery tubes extending from the reservoir through a distal end of the body to provide a pathway for the one or more drugs to exit the reservoir and enter the inner ear.

9. The securable inner ear drug delivery plug of claim 8, wherein the opening in the inner ear is a natural opening comprising a membrane, and wherein the one or more drug delivery tubes have a distal configuration and a longitudinal rigidity to penetrate the membrane.

10. The securable inner ear drug delivery plug of claim 8, wherein an inner surface of each of the one or more drug delivery tubes has a surfactant to control a rate of release of the one or more drugs from the reservoir.

11. The securable inner ear drug delivery plug of claim 6, wherein the reservoir is refillable.

12. The securable inner ear drug delivery plug of claim 11, wherein the body includes a syringe port for re-filling of the reservoir.

13. The securable inner ear drug delivery plug of claim 7, wherein the reservoir is configured to be refillable with one or more of a liquid drug or a solid drug configured to change forms when placed in contact with inner ear fluid via a permeable membrane.

14. The securable inner ear drug delivery plug of claim 7, wherein the membrane is a bioresorable membrane.

15. The securable inner ear drug delivery plug of claim 7, wherein the membrane is a permeable membrane.

16. The securable inner ear drug delivery plug of claim 15, wherein the permeable membrane is configured to change from a sealed form to a permeable form as a result of contact with inner ear fluid within the inner ear of the recipient.

17. The securable inner ear drug delivery plug of claim 15, wherein the permeable membrane is configured to change from a sealed form to a permeable form in response to a temperature change induced by the inner ear of the recipient.

18. A method, comprising:
inserting a drug delivery plug into a recipient, wherein the drug delivery plug includes a body with an elongate frustoconical shape and screw threads extending along an outer surface of the body;
screwing the screw threads into an opening in an inner ear of the recipient such that screw threads mechanically mate with a surface of an inner ear structure surrounding the inner ear opening so as to fluidically seal the inner ear opening and prevent egress of inner ear fluid through the inner ear opening past the screw threads; and
passively releasing a drug from the drug delivery plug directly into the inner ear.

19. The method of claim 18, wherein the drug delivery plug includes a reservoir in the body in which the drug is disposed and one or more drug delivery tubes extending from the reservoir to provide a pathway for the drug to exit the body.

20. The method of claim 19, wherein the opening in the inner ear of a recipient is a natural opening comprising a membrane, and wherein the method further comprises:
penetrating the membrane with the one or more drug delivery tubes during insertion of the drug delivery plug into the opening.

21. The method of claim 19, wherein the drug delivery plug comprises a membrane positioned at a distal end of the reservoir, wherein the membrane is configured to seal the reservoir during insertion of the body into the opening and to allow release of the one or more drugs after insertion of the body into the opening.

22. The method of claim 21, wherein the membrane is a bioresorable membrane.

23. The method of claim 21, wherein the membrane is a permeable membrane.

24. The method of claim 23, wherein the permeable membrane is configured to change from a sealed form to a permeable form as a result of contact with inner ear fluid within the inner ear of the recipient.

25. The method of claim 23, wherein the permeable membrane is configured to change from a sealed form to a permeable form in response to a temperature change induced by the inner ear of the recipient.

* * * * *